United States Patent
Kokare et al.

(10) Patent No.: US 9,708,352 B2
(45) Date of Patent: Jul. 18, 2017

(54) ECHOTHIOPHATE IODIDE PROCESS

(71) Applicant: SHILPA MEDICARE LIMITED, Rajendra Gunj, Raichur, Karnataka (IN)

(72) Inventors: Nagnnath Kokare, Raichur (IN); Venkatanarayana Bathula, Raichur (IN); Akshaykant Chaturvedi, Raichur (IN)

(73) Assignee: SHILPA MEDICARE LIMITED, Karnataka ( * ) Notice: Subject to any disclaimer, the term of this patent is extended or adjusted under 35 U.S.C. 154(b) by 0 days.

(21) Appl. No.: 15/108,790

(22) PCT Filed: Jan. 1, 2015

(86) PCT No.: PCT/IB2015/050008
§ 371 (c)(1),
(2) Date: Jun. 29, 2016

(87) PCT Pub. No.: WO2015/114470
PCT Pub. Date: Aug. 6, 2015

(65) Prior Publication Data
US 2017/0002031 A1 Jan. 5, 2017

(30) Foreign Application Priority Data
Jan. 31, 2014 (IN) .............................. 451/CHE/2014

(51) Int. Cl.
*C07F 9/202* (2006.01)
*C07F 9/17* (2006.01)

(52) U.S. Cl.
CPC ............... *C07F 9/202* (2013.01); *C07F 9/17* (2013.01); *C07B 2200/13* (2013.01)

(58) Field of Classification Search
CPC ...................................................... C07F 9/202
See application file for complete search history.

(56) References Cited

U.S. PATENT DOCUMENTS 2,911,430 A 11/1959 Howard et al.

OTHER PUBLICATIONS

Xinyuan et al, Synthesis of Ecothiapate Iodide,Journal, Chinese journal, yiyao gongye, issue 5, pp. 6-8, year 1984.

*Primary Examiner* — Golam M M Shameem

(57) ABSTRACT

The present invention relates to a process for preparation of Echothiophate Iodide (I). Echothiophate Iodide (I) obtained by the process of the present invention is obtained as new crystalline form designated as Form-SET.

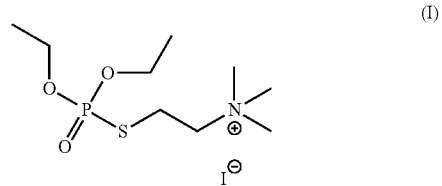

The process for preparation of Echothiophate Iodide (I) according to present invention is an ecofriendly process that avoids the use of hazardous solvent systems and provides Echothiophate Iodide (I) of high purity. Pharmaceutical composition of the said crystalline Form-SET of Echothiophate Iodide (I) of high purity is useful in the treatment of ocular disorders like Glaucoma.

7 Claims, 2 Drawing Sheets

ECHOTHIOPHATE IODIDE PROCESS

FIELD OF THE INVENTION

The present invention relates to a process for preparation of Echothiophate Iodide (I). Echothiophate Iodide (I) obtained by the process of the present invention is obtained as new crystalline form designated as Form-SET.

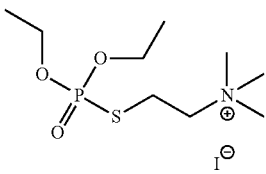

The process for preparation of Echothiophate Iodide (I) according to present invention is an ecofriendly process that avoids the use of hazardous solvent systems and provides Echothiophate Iodide (I) of high purity. Pharmaceutical composition of the said crystalline Form-SET of Echothiophate Iodide (I) of high purity is useful in the treatment of ocular disorders like Glaucoma.

INTRODUCTION

Echothiophate Iodide (I) is chemically known as (2-mercaptoethyl) trimethyl ammonium iodide O,O-diethyl phosphorothioate and is available commercially as Phospholine Iodide®.

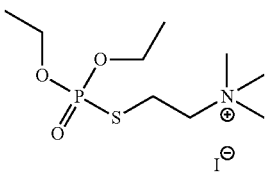

Echothiophate iodide is indicated as ocular antihypertensive agent—for treatment of Glaucoma such as chronic open-angle glaucoma, subacute or chronic angle-closure glaucoma after iridectomy or where surgery is refused or contraindicated and certain non-uveitic secondary types of glaucoma, especially glaucoma following cataract surgery. It is also used for treatment of concomitant esotropias with a significant accommodative component.

Echothiophate iodide is a long-acting cholinesterase inhibitor for topical use which enhances the effect of endogenously liberated acetylcholine in iris, ciliary muscle, and other parasympathetically innervated structures of the eye. It thereby causes miosis, increase in facility of outflow of aqueous humor, fall in intraocular pressure, and potentiation of accommodation. Echothiophate iodide is also found to depresses both plasma and erythrocyte cholinesterase levels in most patients after a few weeks of eye-drop therapy.

Echothiophate iodide occurs as a white, crystalline, water-soluble, hygroscopic solid having a slight mercaptan-like odor. When freeze-dried in the presence of potassium acetate, the mixture appears as a white amorphous deposit.

Very limited literature is available in context of preparation of Echothiophate Iodide. Howard et al in U.S. Pat. No. 2,911,430 disclosed a process for preparation of Echothiophate Iodide by reaction of β-dimethylaminoethylmercaptan hydrochloride with diethylchlorophosphate in benzene solvent, however, it does not provide adequate information as to how to recover the Echothiophate Iodide.

Chinese journal, *Yiyao Gongye*, Issue: 5, Pages: 6-8, 1984; in literature article titled: 'Synthesis of Echothiophate Iodide' provided preparation of Echothiophate Iodide involving reaction of $(EtO)_2PSCl$ and $HOCH_2CH_2NMe_2$, wherein also the solvent system used is benzene, but fails to provide adequate clarity to recover the Echothiophate Iodide as material in hand.

Though the review of the above mentioned literature discloses some preliminary information about process for preparation of Echothiophate Iodide, but the said processes are found to be not particularly convenient and amenable to industrial scale-up, as they suffer from the disadvantage of using carcinogenic solvent benzene besides recovering difficulties of the active drug substance. Thus, there exists an apparent need of new improved processes for preparation of Echothiophate Iodide, which may be efficient, cost-effective, industrially scalable and may overcome the drawbacks of prior disclosed processes.

Echothiophate Iodide being an important ophthalmic therapeutic agent, besides additional and improved ways of preparation, development and characterization of new stable crystalline form may be of immense value to pharmaceutical science and the healthcare of patients.

Therefore, inventors of the present application provide a process for preparation of Echothiophate Iodide, which is cost effective, amenable to scale up at industrial level, ecofriendly-avoids use of hazardous chemicals, safer for handling, and provides the pure non-hygroscopic end product in high yield with better and consistent quality parameters. Echothiophate Iodide (I) obtained by the process of the present invention is obtained as crystalline Form-SET, which is stable, pure and easy for handling and further processing for formation of compositions useful for ocular disorders.

SUMMARY OF INVENTION

Particular aspects of the present specification relate to the process for the preparation of Echothiophate Iodide (I).

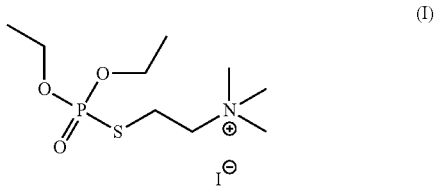

The process of preparation of Echothiophate Iodide (I) comprises the steps of-
  a) providing a solution of 2-(dimethylamino) ethane thiol or its salt and a base in an organic solvent;
  b) optionally heating the reaction mixture to 50-70° C. and obtaining a residual mass;
  c) treating the step a) or b) material with diethyl halogen phosphate in an organic solvent having boiling point greater than 100° C. to obtain S-2-(dimethyl amino) ethyl O,O-diethyl phosphorothioate of Formula (II);

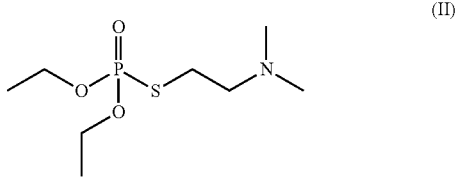

(II)

d) reacting S-2-(dimethyl amino)ethyl O,O-diethyl phosphoro thioate (II) of step c) with methyl iodide in an organic solvent;

e) isolating pure Echothiophate Iodide (I).

Isolation of pure Echothiophate Iodide (I) as mentioned in the above process according to present invention further comprises the steps of:

i. providing a solution of reaction mass obtained from step d) in 2-5 volume $C_1$-$C_3$ alcohol solvent;
  ii. recovering solvent from reaction mixture to obtain a residue;
  iii. treating the residue obtained in step ii. with an ester solvent;
  iv. isolating the pure Echothiophate Iodide (I).

The process for preparation of Echothiophate Iodide according to present invention is cost effective, amenable to scale up at industrial level, avoids use of hazardous chemicals and provides the pure non-hygroscopic end product in high yield.

Another aspect of the present invention provides that Echothiophate Iodide (I) obtained by the process of the present invention is obtained as crystalline Form-SET, characterized by X-ray powder diffraction pattern—having at least five $2\theta°$ peaks selected from the XRPD peak set of 14.4, 15.0, 18.2, 18.7, 21.1, 21.3, 23.3, 25.1 and $31.8\pm0.2\theta°$; or substantially according to FIG. 1.

Further, Echothiophate Iodide (I) prepared according to the process of the present invention is non-hygroscopic in nature and having assay by potentiometric titration method in between 95% to 102% w/w. The melting point of Echothiophate Iodide (I) prepared according to the process of the present invention ranging between 106-114° C. (capillary method) and DSC isotherm having an endothermic peak in ranging between 122-128° C.

Further particular aspects of the invention are detailed in the description part of the specification, wherever appropriate.

ABBREVIATIONS

Figure 1:
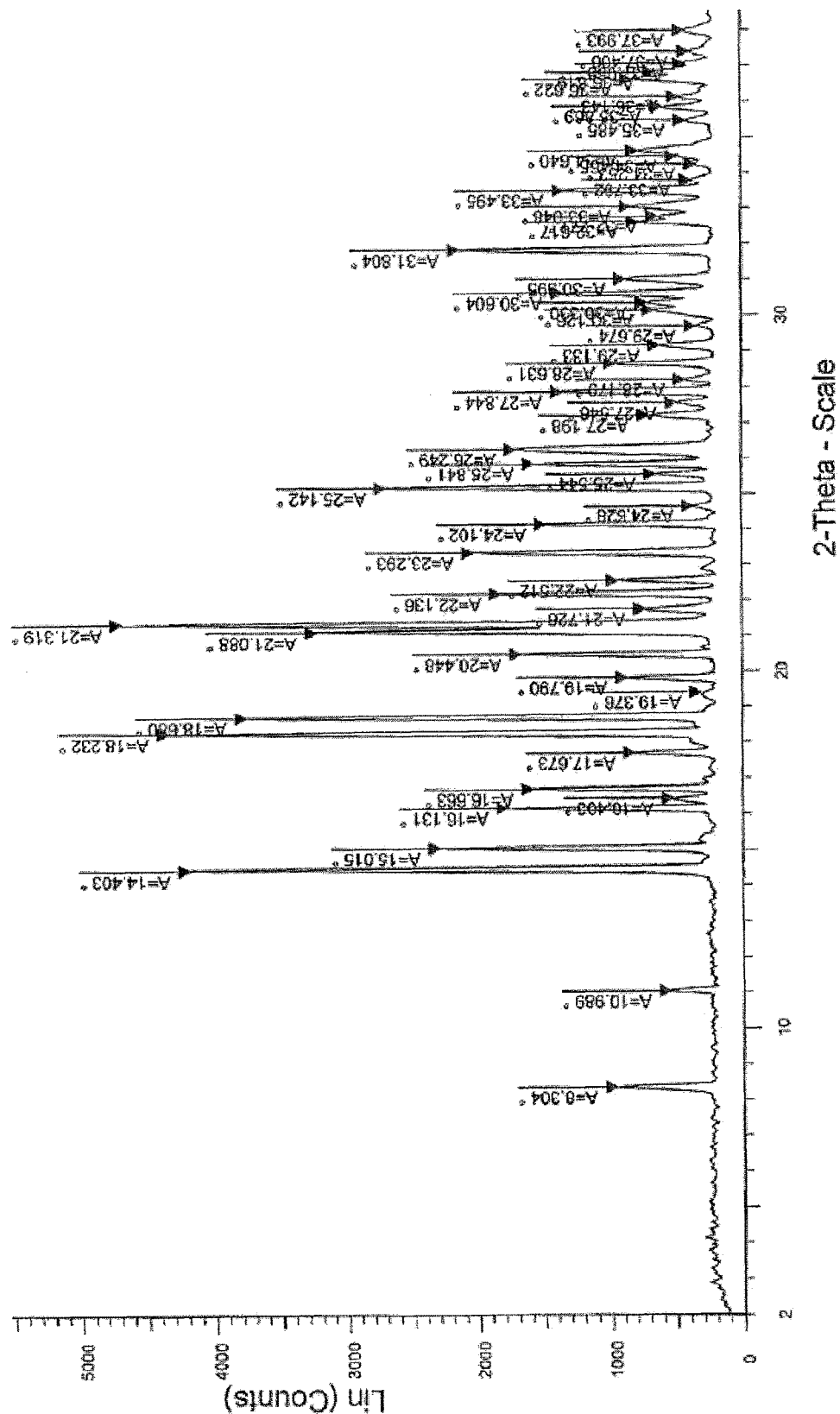
FIG. 1 is illustration of X-ray powder diffraction ("XRPD") pattern of crystalline Echothiophate Iodide (I), designated as Form-SET.

| API | Active Pharmaceutical Ingredient |
|---|---|
| HPLC | High-Performance Liquid Chromatography |
| RT | Room Temperature |
| XRPD | X-Ray Powder Diffraction Pattern |

DETAILED DESCRIPTION

As set forth herein, embodiments of the present invention relate to a process for the preparation of Echothiophate Iodide (I),

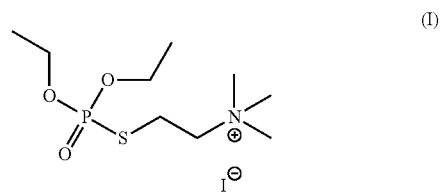

(I)

comprising the steps of:
  a) providing a solution of 2-(dimethylamino) ethane thiol or its salt and a base in an organic solvent;
  b) optionally heating the reaction mixture to 50-70° C. and obtaining a residual mass;
  c) treating the step a) or b) material with diethyl halogen phosphate in an organic solvent having boiling point greater than 100° C. to obtain S-2-(dimethyl amino) ethyl O,O-diethyl phosphorothioate of Formula (II);

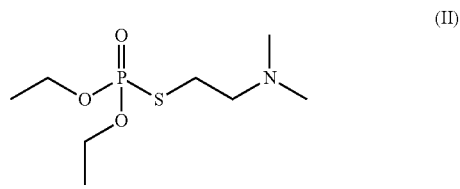

(II)

d) reacting S-2-(dimethyl amino)ethyl O,O-diethyl phosphoro thioate (II) of step c) with methyl iodide in an organic solvent;
  e) isolating pure Echothiophate Iodide (I).

The individual steps of the process according to the present invention for preparing Echothiophate Iodide (I) are detailed separately herein below.

Step a) comprises providing a solution of 2-(dimethylamino) ethanethiol or its salt and a base in an organic solvent; Organic solvent used in this reaction is preferably a $C_1$-$C_3$ alcoholic solvent selected from methanol, ethanol or n-propanol. Any conventional base may be used to perform this reaction. In one of the embodiment of the present invention, the base is selected from alkali metal alkoxide and may be optionally be prepared in situ also, by addition of Na metal to the reaction mixture containing alcoholic solvent. The amount of solvent used in this step ranges from 8-15 times in volume w.r.t. weight of 2-(dimethylamino) ethanethiol or its salt.

Any salt of 2-(dimethylamino) ethanethiol may be used as starting material for this reaction. In a preferred embodiment 2-(dimethylamino) ethanethiol is used as its hydrochloride salt. In an embodiment of the present invention, a solution of 2-(dimethylamino) ethanethiol or its salt is added to base-organic solvent mixture in a dropwise manner maintaining the temperature between 25-35° C.

Step b) comprises optionally heating the reaction mixture to 50-70° C. and obtaining a residual mass;

The reaction mixture obtained in step a) is optionally heated to a temperature of 50-70° C., where it may be maintained for time of 30 mins to 2 hrs and then by removing solvent under reduced pressure, the residual mass is obtained.

Step c) comprises treating the step a) or b) material with diethyl halogen phosphate in an organic solvent having boiling point greater than 100° C. to obtain S-2-(dimethyl amino) ethyl O,O-diethyl phosphorothioate of Formula (II);

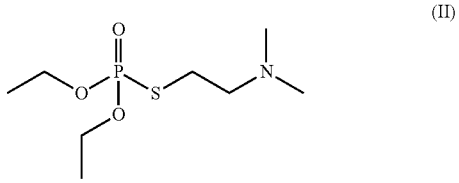

(II)

In a preferred embodiment of the present invention, diethylhalogenphosphate is selected to be diethylchlorophosphate. The solvent system used for this reaction comprises a solvent with boiling point greater than 100° C. In an embodiment of the present invention, solvent with boiling point greater than 100° C. is selected from toluene or xylene. The reaction is initially carried out at low temperature of 0-10° C. wherein diethylhalogenphosphate is added slowly to the reaction mixture in a drop wise manner so that reaction mass temperature is maintained at below 15° C.

After addition of diethylhalogenphosphate, the reaction mixture is warmed to 35-40° C., wherein stirring may be performed for time duration ranging from 1-4 hrs. Progress of the reaction as is intermittently checked. On completion of reaction, after suitable work-up known to the person skilled in the art S-2-(dimethylamino)ethyl O,O-diethyl phosphorothioate of Formula (II) is isolated from the reaction mixture as an oily compound.

With increasing emphasis on safety of the pharmaceutical substances, regulatory agencies demand stringent in process mechanisms for determination and the control of DNA reactive (mutagenic) impurities/genotoxic impurities in medicinal products. Use of solvent with boiling point greater than 100° C. in this reaction substantiates the inventive merit of present invention wherein use of hazardous and carcinogenic solvents like benzene is obviated, and a safer and better alternative has been provided.

Step d) comprises reacting S-2-(dimethylamino)ethyl O,O-diethyl phosphorothioate (II) obtained in step c) with methyl iodide in a an organic solvent selected from a nitrite or ketone solvent for e.g. acetonitrile or acetone. Amount of organic solvent used ranges from 4-10 times (by volume), w.r.t. the weight of S-2-(dimethylamino)ethyl O,O-diethyl phosphorothioate (II) (in g).

The reaction is carried out at low temperature of 0-10° C. wherein methyl iodide is added slowly to the reaction mixture in a drop wise manner so that reaction mass temperature is maintained at below 10° C. After completion of the addition, reaction mixture is allowed to attain RT and stirred for time duration of 8-16 hrs. Progress of the reaction as is intermittently checked by HPLC.

On completion of reaction, the precipitates are optionally filtered, treated with a polar organic solvent like acetonitrile, ethyl acetate, isopropanol etc. and dried to obtain a solid material i.e. crude Echothiophate Iodide.

Step e) comprises isolating pure Echothiophate Iodide (I).

Crude Echothiophate Iodide obtained in step d) is provided as solution in 2-5 volume $C_1$-$C_3$ alcohol solvent selected from methanol, ethanol or isopropanol. Reaction is carried out at RT, by stirring to get clear solution. The solvent may be recovered from reaction mixture to under reduced pressure conditions to obtain a residue. The residue obtained is then treated with an ester solvent selected from methyl acetate, ethyl acetate, propyl acetate, isopropyl acetate or methyl propionate to get a solid material. Pure Echothiophate Iodide (I) is finally obtained by drying the solid material under reduced pressure conditions like vacuum.

Process of isolating pure Echothiophate Iodide (I) may further comprise processes but not limited to conventional processes including scrapping and if required filtering from slurry which may be carried out at room temperature for the suitable durations.

The process related impurities that appear in the impurity profile of pure Echothiophate Iodide (I) may be substantially removed by the process of the present invention resulting in the formation of pure Echothiophate Iodide (I) in a crystalline form. Substantially pure Echothiophate Iodide (I) obtained according to the process of the present invention results in the final API having assay by potentiometric titration method in between 95% to 102% w/w.

The merit of the process according to the present invention resides in that—crystalline product obtained after drying is very stable, non-hygroscopic and may be suitably stored for prolonged durations.

The crystalline Echothiophate Iodide (I), obtained according to the process of the present invention is characterized by X-ray powder diffraction pattern substantially according to FIG. 1. The Echothiophate Iodide (I) obtained by the process of the present invention is obtained as crystalline Form-SET, characterized by X-ray powder diffraction pattern—having at least five 2θ° peaks selected from the XRPD peak set of 14.4, 15.0, 18.2, 18.7, 21.1, 21.3, 23.3, 25.1 and 31.8±0.2θ°. The melting point of Echothiophate Iodide (I) prepared according to the process of the present invention ranging between 106-114° C. (capillary method) and DSC isotherm having an endothermic peak in ranging between 122-128° C.

The characteristic peaks and the corresponding d-spacing values of the crystalline Form-SET of Echothiophate Iodide (I), obtained by the process of the present invention are tabulated in the Table-1.

TABLE 1

| S. No. | Angle (2θ°) ± 0.20 | d-Spacing Value (A°) |
|---|---|---|
| 1. | 14.40 | 6.144 |
| 2. | 15.02 | 5.895 |
| 3. | 16.13 | 5.490 |
| 4. | 16.66 | 5.316 |
| 5. | 18.23 | 4.862 |
| 6. | 18.70 | 4.746 |
| 7. | 20.45 | 4.339 |
| 8. | 21.09 | 4.209 |
| 9. | 21.32 | 4.164 |
| 10. | 22.14 | 4.012 |
| 11. | 23.30 | 3.815 |
| 12. | 24.10 | 3.689 |
| 13. | 25.14 | 3.539 |
| 14. | 25.84 | 3.445 |
| 15. | 26.25 | 3.392 |
| 16. | 27.85 | 3.201 |
| 17. | 30.60 | 2.918 |
| 18. | 31.80 | 2.811 |
| 19. | 33.50 | 2.673 |

Minor variations in the observed 2 θ° angles values may be expected based on the analyst person, the specific XRPD diffractometer employed and the sample preparation technique. Further possible variations may also be expected for the relative peak intensities, which may be largely affected by the non-uniformity of the particle size of the sample. Hence, identification of the exact crystalline form of a compound should be based primarily on observed 2 theta angles with lesser importance attributed to relative peak intensities. The 2 theta diffraction angles and corresponding d-spacing values account for positions of various peaks in the X-ray powder diffraction pattern. D-spacing values are calculated with observed 2 theta angles and copper K a wavelength using the Bragg equation well known to those of having skill in the art of XRPD diffractometry science.

Figure 2:
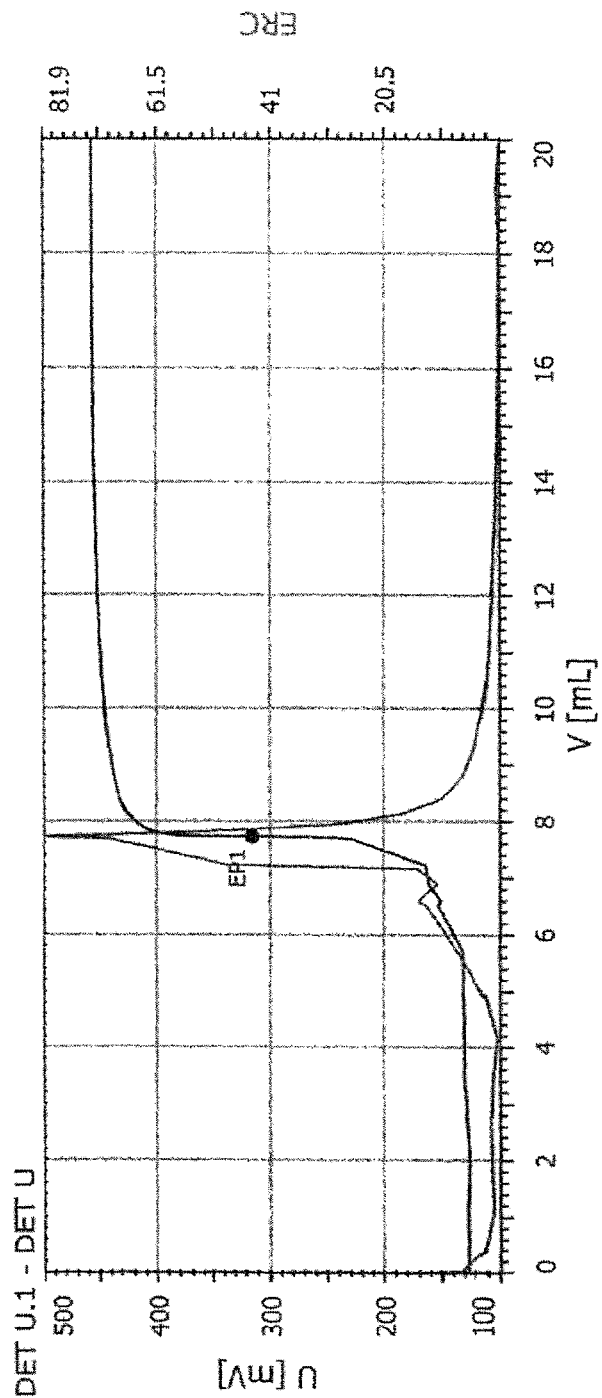
FIG. 2 is illustration of assay determination by Potentiometric titrimetric method of Echothiophate Iodide (I) obtained according to the process of the present invention.

The samples of crystalline Form-SET of Echothiophate Iodide (I) described herein were analyzed by XRPD on a Bruker AXS D8 Advance Diffractometer using X-ray source —Cu Kα radiation using the wavelength 1.5418 Å and lynx Eye detector. Illustrative examples of analytical data for Echothiophate Iodide (I) obtained in the example is set forth in the FIGS. 1 and 2.

Crystalline Form-SET of Echothiophate Iodide (I) is suitable for handling and further processing is achieved directly by the process of the present invention. Thus process of the present invention has advantage of directly providing the material suitable for making pharmaceutical compositions.

In another embodiment, the Echothiophate Iodide Form-SET obtained by the processes of the present application may be formulated as compositions wherein the active product is mixed with one or more pharmaceutically acceptable excipients. They may also be prepared in the form of sterile compositions, which can be dissolved at the time of use in sterile water or any other sterile medium. Pharmaceutical composition of the said crystalline Form-SET of Echothiophate Iodide (I) of high purity is useful in the treatment of ocular disorders like Glaucoma.

EXAMPLES

Example-1

Process for Preparation of Echothiophate Iodide (I).

General process for preparation of Echothiophate Iodide (I) according to a preferred embodiment of the present invention is outlined below:

The individual steps of the above process according to the present invention are detailed herein:

Stage-I: Preparation of S-2-(dimethylamino)ethyl O,O-diethyl phosphorothioate 80 mL methanol was charged to a three neck 250 mL clean and dry Round Bottom Flask (RBF) equipped with water condenser. Slowly over a period of 30 mins, added 4.1 g sodium metal pieces to methanol maintaining temperature below 40° C. The reaction mixture was stirred for 30 mins to get clear solution. Solution of 10 g 2-(dimethyl amino) ethane thiol hydrochloride in 40 ml methanol was added drop wise to reaction mass while maintaining temperature of 25-30° C. The reaction mixture was then heated to 60-65° C. and maintained for about 1 hr. The reaction mixture was then cooled and subjected to distillation to recover the solid residue.

To the recovered residue 100 mL toluene was charged and the reaction mass was cooled to 0-5 ° C. Then 12.2 g diethyl chloro phosphate was added drop wise over a period of 30 mins to the reaction mixture while maintaining reaction mass temperature at 10-15° C. The reaction mixture was then warmed to 40° C. and stirred for about 2-3 hrs.

About 60 mL aqueous solution was charged to reaction mass and stirring done for about half an hour. Later on, aqueous portion was separated and washed thrice with 40 mL toluene. Organic layer was combined, dried over sodium sulfate, filtered and distilled completely under vacuum to get 15 g oily compound.

Stage-II: Preparation of Echothiophate Iodide (Crude).

S-2-(dimethyl amino)ethyl O,O-diethyl phosphoro thioate (15 g) and 75 mL acetonitrile were charged to three neck 250 mL clean and dry RBF. The reaction mixture was cooled to 0-10° C. and 20 g methyl iodide was added drop wise over a period of 30 mins maintaining reaction mass temperature below 10° C. After the completion of addition, reaction mass was allowed to attain room temperature and stirred for about 14 hrs.

The precipitated product was filtered and washed with 20 mL acetonitrile. Filtrate was distilled under vacuum at temperature below 50° C. and 20 mL ethyl acetate was added to the residue followed by complete solvent removal by distillation. Then 10 mL isopropanol and 80 mL ethyl

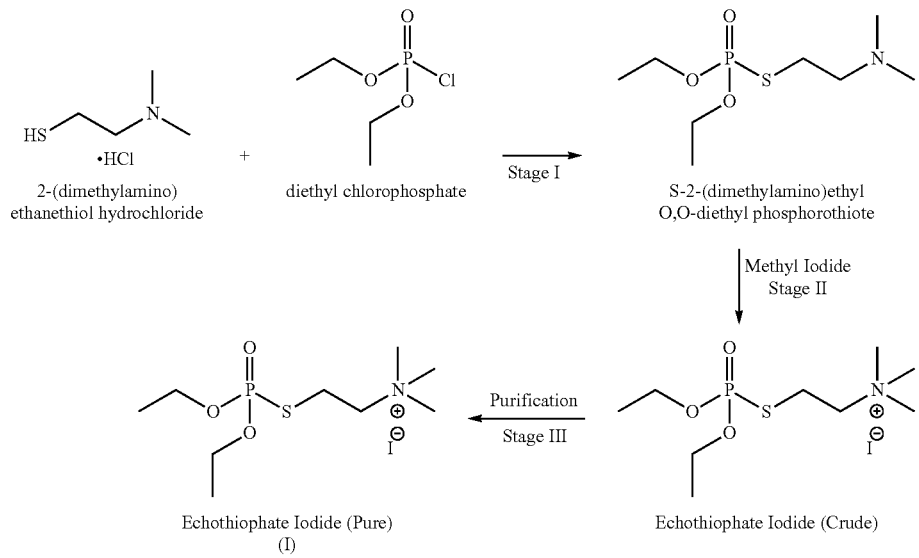

acetate were added to the reaction mass and stirred for about 1 hr at room temperature. The precipitated solid was filtered on Buchner funnel, washed with 20 mL ethyl acetate and dried at 50° C. under vacuum for 2-3 hrs to obtain 15 g crude Echothiophate Iodide.

Stage-III: Purification of Crude Echothiophate Iodide 15 g crude Echothiophate Iodide and 45 mL methanol were added to a 250 mL clean and dry RBF at RT. The reaction mass was stirred at room temperature for 15 min to get clear solution. The reaction mixture was filtered through micron filter paper and washing was given with 15 mL methanol.

The collected methanol filtrate was distilled completely at below 40° C. under vacuum to get residue, to which 450 mL ethyl acetate was added and stirring performed for 1 hr at RT. The precipitated solid was filtered on Buchner funnel and washed with 15 ml ethyl acetate. The solid material obtained was dried at 55° C. under vacuum for 10 hrs, to obtain 13 gm, pure Echothiophate [Assay by potentiometric titration method in between 95 to 102% w/w] in a crystalline form designated as Form-SET, having the XRPD diffractogram as shown in FIG. 1.

While the foregoing pages provide a detailed description of the preferred embodiments of the invention, it is to be understood that the description and examples are illustrative only of the principles of the invention and not limiting. Furthermore, as many changes can be made to the invention without departing from the scope of the invention, it is intended that all material contained herein be interpreted as illustrative of the invention and not in a limiting sense.

We claim:

1. A process for preparation of Echothiophate Iodide (I),

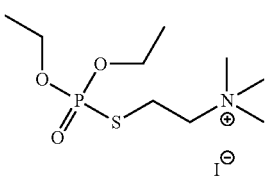

(I)

comprising the steps of:
a) providing a solution of 2-(dimethylamino) ethane thiol or its salt and a base in an organic solvent;
b) optionally heating the reaction mixture to 50-70° C. and obtaining a residual mass;
c) treating the step a) or b) material with diethyl halogen phosphate in an organic solvent having boiling point greater than 100° C. to obtain S-2-(dimethyl amino) ethyl O,O-diethyl phosphorothioate of Formula (II);

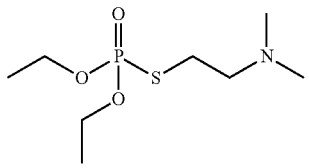

(II)

d) reacting S-2-(dimethyl amino)ethyl O,O-diethyl phosphoro thioate (II) of step c) with methyl iodide in an organic solvent; and
e) isolating pure Echothiophate Iodide (I).

2. A process for preparation of Echothiophate Iodide (I) according to claim 1, wherein organic solvent used in step a) is $C_1$-$C_3$ alcoholic solvent selected from methanol, ethanol or n-propanol and the base is an alkali metal alkoxide.

3. A process for preparation of Echothiophate Iodide (I) according to claim 1, wherein in step c) diethyl halogen phosphate is selected to be diethylchlorophosphate and solvent with boiling point greater than 100° C. is hydrocarbon solvent selected from toluene or xylene.

4. A process for preparation of Echothiophate Iodide (I) according to claim 1, wherein organic solvent used in step d) is a nitrile or ketone solvent selected from acetonitrile or acetone.

5. A process for preparation of Echothiophate Iodide (I) according to claim 1, wherein in step e) isolation of pure Echothiophate Iodide (I) further comprises the steps of:
i. providing a solution of reaction mass obtained from step d) in 2-5 volume $C_1$-$C_3$ alcohol solvent selected from methanol, ethanol or isopropanol;
ii. recovering solvent from reaction mixture to obtain a residue;
iii. treating the residue obtained in step ii. with an ester solvent selected from methyl acetate, ethyl acetate, propyl acetate, isopropyl acetate or methyl propionate; and
iv. isolating the pure Echothiophate Iodide (I).

6. Crystalline Echothiophate Iodide (I), designated as Form-SET characterized by X-ray powder diffraction pattern- having at least five 2θ° peaks selected from the XRPD peak set of 14.4, 15.0, 18.2, 18.7, 21.1, 21.3, 23.3, 25.1 and 31.8±0.2θ°.

7. Crystalline Echothiophate Iodide (I) Form-SET, according to claim 6, further characterized by X-ray powder diffraction pattern- having diffraction angle 2θ° peaks at 16.1, 16.7, 20.4, 22.1, 24.1, 25.8, 26.2, 27.8, 30.6 and 33.5±0.2θ°.

* * * * *